United States Patent [19]

Green et al.

[11] Patent Number: 5,709,210

[45] Date of Patent: Jan. 20, 1998

[54] ULTRASOUND SYSTEM FOR IMAGING

[75] Inventors: J. Michael Green, Pleasanton; Bhaskar Ramamurthy, Santa Clara, both of Calif.

[73] Assignee: Acuson Corporation, Mountain View, Calif.

[21] Appl. No.: 692,865

[22] Filed: Jul. 30, 1996

[51] Int. Cl.$^6$ ..................................................... A61B 8/00
[52] U.S. Cl. ..................................................... 128/661.07
[58] Field of Search .................. 128/660.04, 660.05, 128/660.06, 660.07, 661.04, 661.07, 661.08, 661.09, 661.1, 916

[56] References Cited

U.S. PATENT DOCUMENTS

| | | | |
|---|---|---|---|
| 5,099,847 | 3/1992 | Powers et al. | 128/660.07 |
| 5,148,810 | 9/1992 | Maslak et al. | |
| 5,188,112 | 2/1993 | Sturgill et al. | |
| 5,211,169 | 5/1993 | Freeland. | |
| 5,233,994 | 8/1993 | Shmulewitz. | |
| 5,285,788 | 2/1994 | Arenson et al. | 128/660.06 |
| 5,431,161 | 7/1995 | Ryals et al. | |
| 5,533,510 | 7/1996 | Koch, III et al. | 128/660.07 |

OTHER PUBLICATIONS

*New Quantitation of Approaches to Contrast Enhancement*, Armstrong et al., University of Michigan, Ann Arbor, Michigan, Jun. 1996.

*Innovative Imaging Modalities: Harmonic Imaging, Power Doppler Imaging, and Triggered Mode Imaging: Concepts and Instrumentation*, Powers et al., Advanced Technology Laboratories, Inc., University of Toronto, Jun. 1996.

*Harmonic Imaging and Single Frame "Triggered Mode" Data Acquisition Enhance Delineation of Myocardial Perfusion Defects by Volume–Rendered 3–Dimensional Echocardiography*, Cao et al., Tufts–New England Medical Center, Boston, Massachusetts, Jun. 1996.

*An ECG–Gated Color Doppler Imaging System For Determination of Coronoary Bypass Graft Patency*, Klepper et al., Institute of Applied Physiology and Medicine, pp. 203–212, Apx. 1985.

*Primary Examiner*—George Manuel
*Attorney, Agent, or Firm*—Brinks Hofer Gilson & Lione

[57] ABSTRACT

Color Doppler data is acquired only over a portion of the cardiac cycle, such as during diastole in order to increase the sensitivity of detection. Ultrasound system parameters such as clutter filter coefficience, temporal and spatial filter coefficients may be altered only for a portion of the cardiac cycle to increase detection sensitivity, to improve myocardial border estimation and to avoid the loss of color Doppler image at end-diastole.

91 Claims, 9 Drawing Sheets

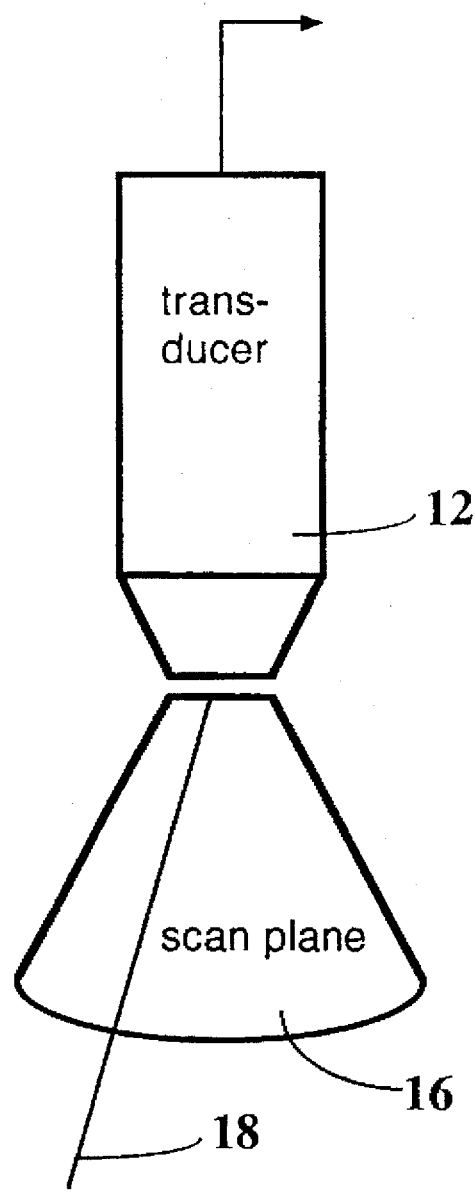
FIG._1.

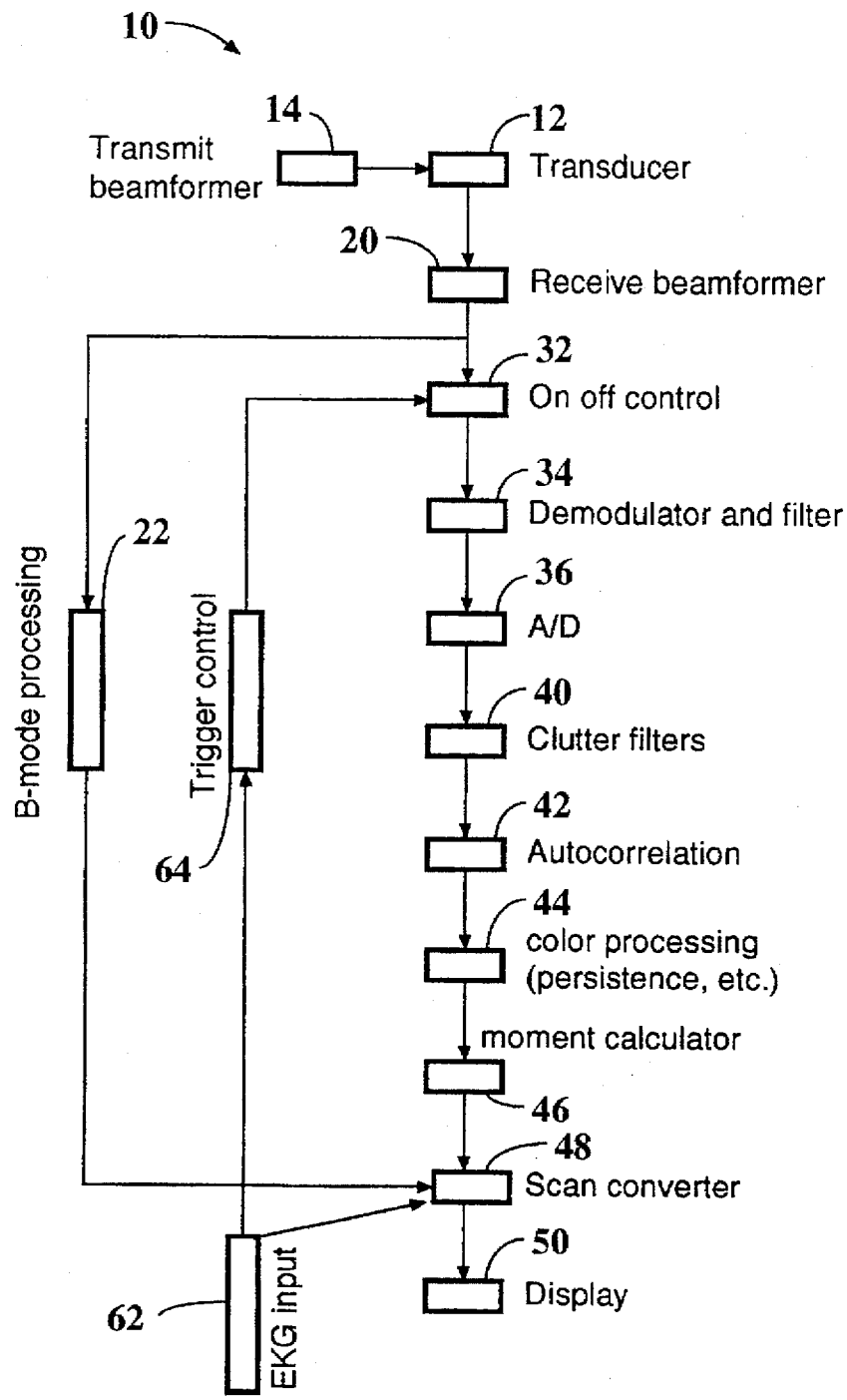
FIG._2A.

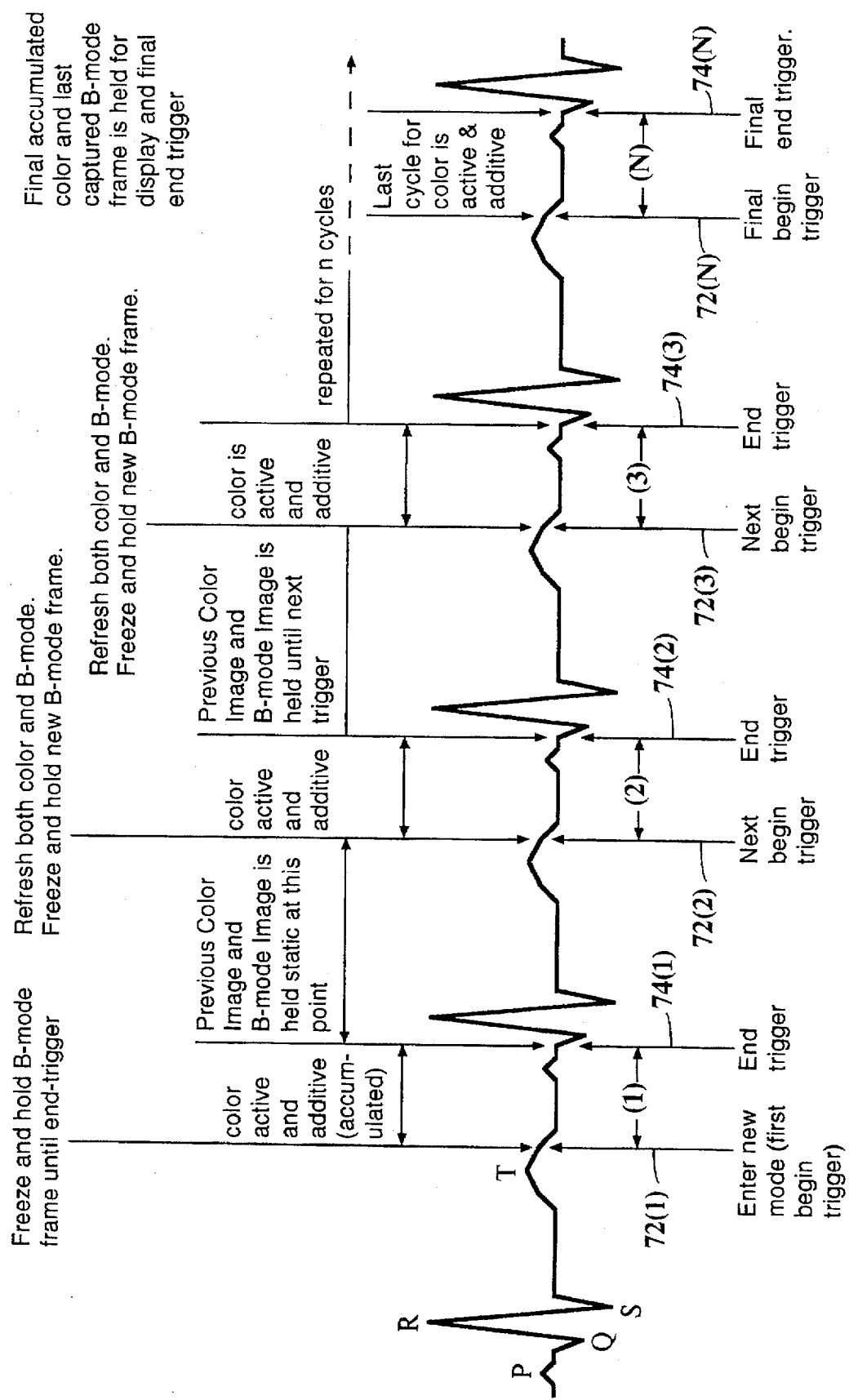
FIG._4C.

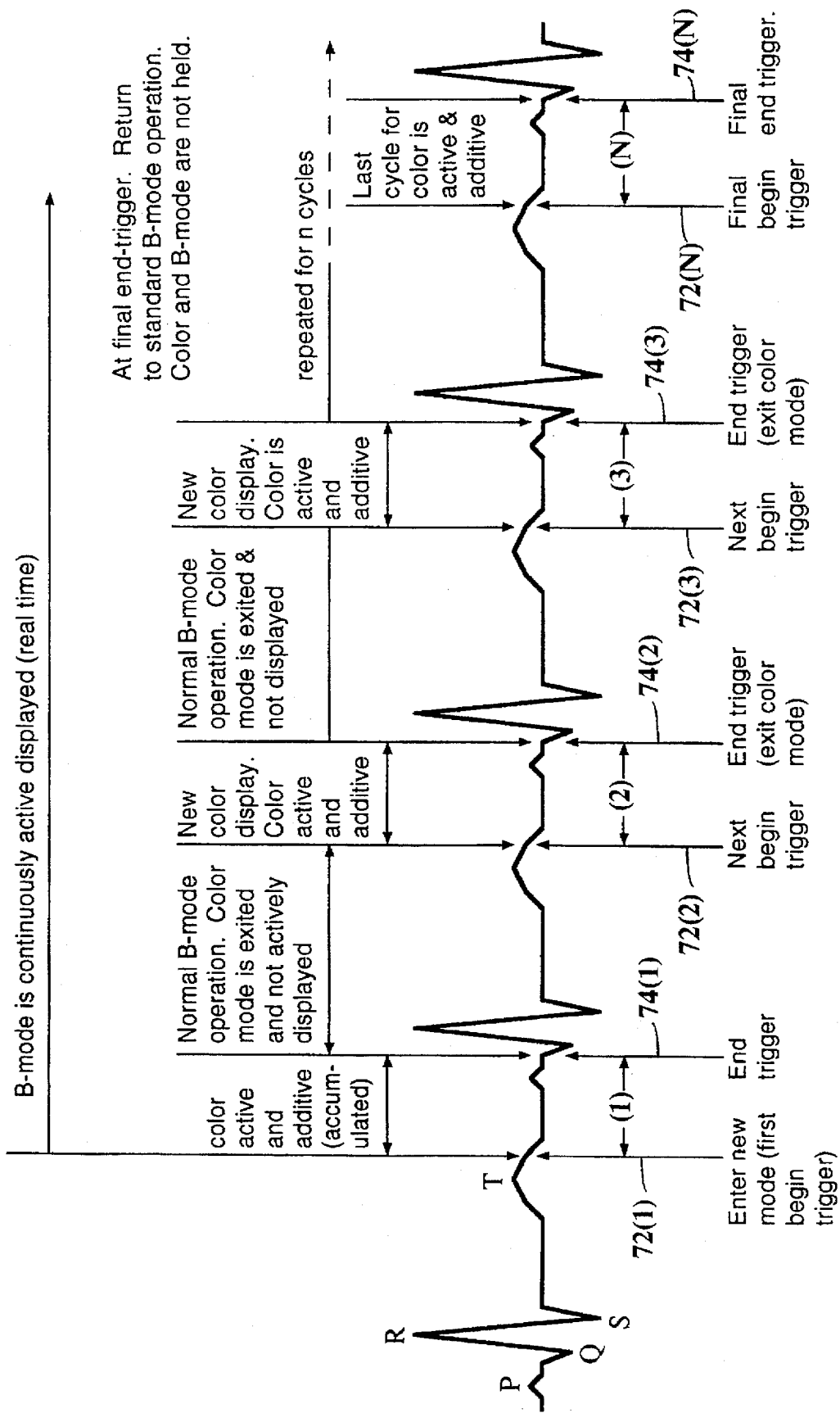
FIG._4D.

ULTRASOUND SYSTEM FOR IMAGING

BACKGROUND OF THE INVENTION

This invention relates in general to ultrasound imaging, and in particular to an ultrasound system for imaging tissue and/or blood flow where the imaging is performed in response to a cardiac cycle, such as that of a human or animal.

In clinical analysis, it is important to determine myocardial perfusion and color Doppler velocity or energy mapping of the ventricles and preservation of intra-cardiac blood pool images. Information on myocardial perfusion would allow the clinician to more accurately diagnose coronary and heart function. Mapping of the ventricles permits improved myocardial border estimations and the preservation of intra-cardiac blood pool images allow the clinician to measure the blood pool.

Previous methods used to determine myocardial perfusion include direct imaging methods such as doubutamine magnetic resonance imaging, thallium-201 imaging, technetium-99 imaging and myocardial contrast echocardiography. Indirect methods look at the velocity or relative motion of the heart wall and include stress echocardiography and Doppler determined wall velocities.

Ventricular angiography is used to determine ventricular borders, ejection fractions and cardiac output.

CD (color Doppler) capture is also currently available for ultrasound imaging systems. Cumulative color Doppler signals over multiple beats are overlaid on a real-time 2-D reference image. As currently implemented, the CD capture function displays the highest mean velocities detected at each point in the image during a selected time interval. Interval options are one, two, four, and eight seconds. Once activated, the display of the highest mean velocity remains on the screen. If a subsequent mean velocity at the same spatial location is of a greater magnitude, it replaces the initial sample. Since color sample points are measures of mean velocity, the display is created by accumulating the maximum (or peak) mean velocities. B-mode is active continuously during the selected intervals and is frozen when the selected interval end-point is reached.

The acquisition of data is unaffected by invoking the CD capture feature, except that when the end of interval is reached the imaging of the acquisition stops. The interval sometimes can also be of indefinite length; in such event the user still specifies a time interval and the CD frames are accumulated for the selected time interval and then a fresh cycle of accumulation starts. This process continues until the user instructs the system to stop. Here too, the acquisition is not controlled.

EKG (electrocardiogram) trigger is currently available on most cardiology ultrasound imaging systems. In its current implementation, one or two separate trigger points are selected along an EKG waveform. In its most usual implementation, the EKG signal triggers the acquisition of one frame of ultrasound data. The data is displayed on the screen till the next trigger comes along and the process is repeated. The acquisition includes transmission, reception and scan conversion of ultrasound data. More than one trigger point is also allowed in some machines. At each trigger point, one frame is acquired. The triggered operation is continued till the feature is de-selected.

There are many disadvantages with the above methods. Current myocardial contrast echocardiography is insensitive and patients experience frequent side effects from the contrast agents. Thallium and technetium scanning involve expensive radioisotopes with short shelf lives. Doubutamine MRI is currently undergoing clinical trials and many patients poorly tolerate MRI examination. Indirect methods fail to differentiate between viable myocardium from stunned or hibernating myocardium and are insensitive and difficult to apply.

Techniques used to determine the cavity area, cross-sectional size or ventricular function, as in the case of ventricular angiography, are expensive and time consuming. Ultrasonic methods to similarly measure and evaluate the cardiac chambers are prone to numerous inaccuracies.

Even though CD (color Doppler) capture is useful for cardiac applications, further improvements can be made. For cardiac applications, it is desirable to be able to select from a range of desired B-mode and color Doppler behaviors and interactions. In CD capture as currently implemented, B-mode and color Doppler image acquisition is halted at the end of a pre-selected interval. This does not allow for serial comparisons of Doppler detected changes over time. Also, CD capture is not triggered by any signals originating from the body. The acquisition and display of CD frames is not synchronized with any events in the body. Currently, the user decides when to activate CD capture, based on his or her understanding of the events that are visualized with B-mode displays.

It is therefore desirable to provide an improved ultrasound imaging system with improved capability for detecting myocardial perfusion, for mapping of the ventricles and for preservation of intra-cardiac blood pool images as well as other imaging functions.

SUMMARY OF THE INVENTION

One aspect of the invention is directed to an ultrasound method for imaging tissue and/or blood flow, comprising the steps of providing a begin trigger indicative of a first point in a cardiac cycle; and acquiring in response to the begin trigger a color Doppler first imaging sequence of multiple frames of color Doppler data at different times in said cardiac cycle.

Another aspect of the invention is directed towards an ultrasound method for imaging tissue and/or blood flow, comprising the steps of providing a trigger responsive to a portion of a cardiac cycle, said portion being shorter than the cardiac cycle. The method further comprises displaying in response to the trigger a color Doppler first imaging sequence of multiple frames of color Doppler data at different times in said cardiac cycle.

Yet another aspect of the invention is directed towards an ultrasound method for imaging tissue and/or blood flow, comprising the steps of acquiring color Doppler data from said tissue and/or blood flow by means of a system with system parameters providing a trigger indicative of a point in the cardiac cycle; and altering the values of said system parameters in response to the trigger so that the acquiring step acquires color Doppler data according to different system parameters at different points of the cardiac cycle.

One more aspect of the invention is directed to an ultrasound apparatus for imaging tissue and/or blood flow, comprising means for providing a begin trigger indicative of a first point in a cardiac cycle; and means for acquiring in response to the begin trigger a color Doppler first imaging sequence of multiple frames of color Doppler data at different times in said cardiac cycle.

Yet another aspect of the invention is directed towards an ultrasound apparatus for imaging tissue and/or blood flow, comprising means for providing a trigger responsive to a portion of a cardiac cycle, said portion being shorter than the cardiac cycle. The apparatus further comprises means for displaying in response to the trigger a color Doppler first imaging sequence of multiple frames of color Doppler data at different times in said cardiac cycle.

Still another aspect of the invention is directed towards an ultrasound apparatus for imaging tissue and/or blood flow, comprising means for acquiring color Doppler data from said tissue and/or blood flow using system parameters; means for providing a trigger indicative of a point in the cardiac cycle; and means for altering the values of said system parameters in response to the trigger so that the acquiring step acquires color Doppler data according to different system parameters at different points of the cardiac cycle.

BRIEF DESCRIPTION OF THE DRAWINGS

FIG. 1 is a block diagram of a transducer of an ultrasound imaging system for imaging tissue and blood flow to illustrate the invention.

FIG. 2A is a block diagram of an ultrasound imaging system for illustrating a first embodiment of the invention.

FIGS. 4B, 4C, and 4D are graphical illustrations of EKG waveforms to illustrate different modes of operation of the system of FIG. 4A.

For simplicity in description, identical components in this application are identified by the same numerals.

DETAILED DESCRIPTION OF THE PREFERRED EMBODIMENT

Figure 2B:
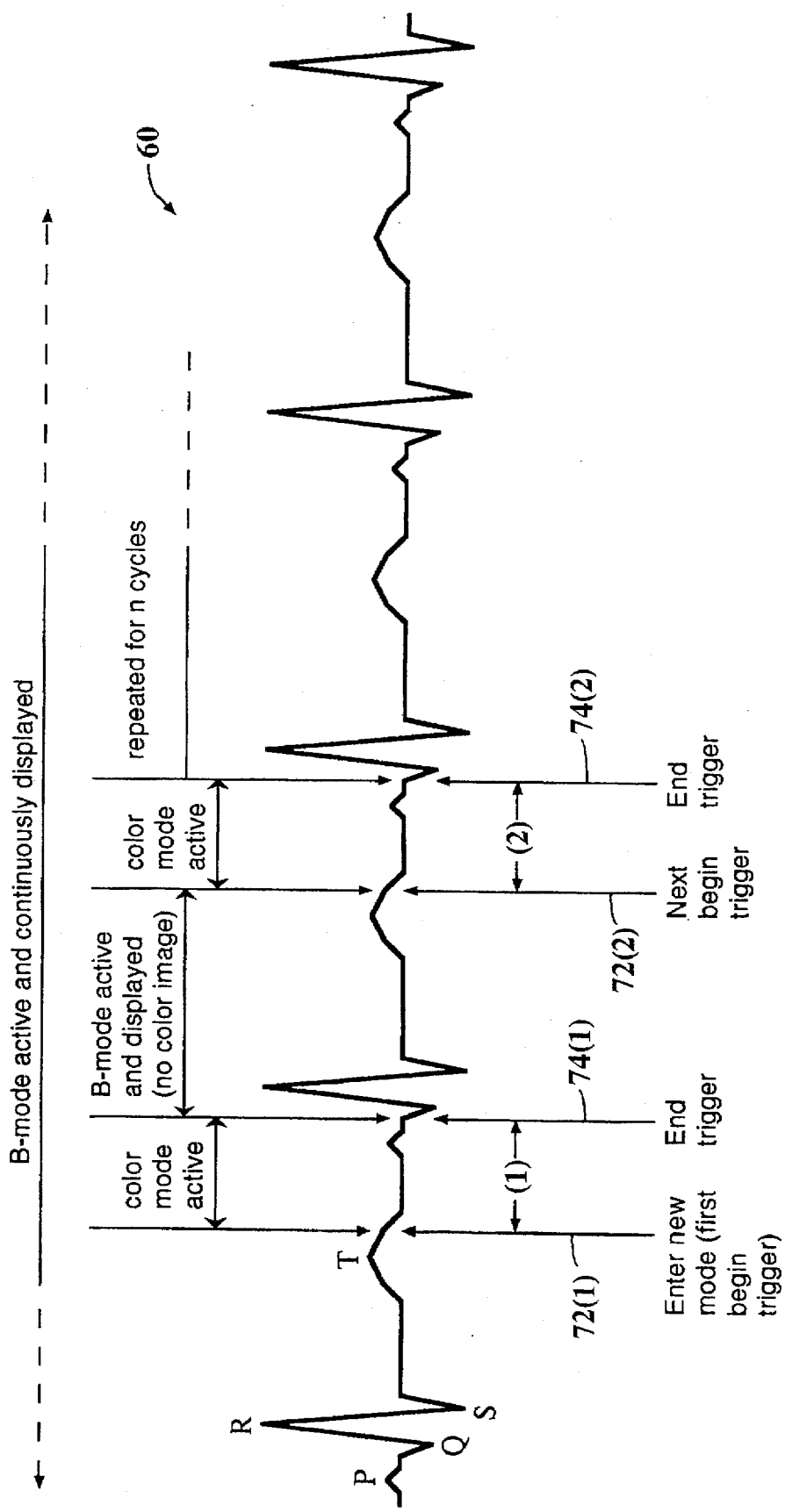
FIG. 2B is a graphical illustration of the EKG waveform to illustrate the operation of the system of FIG. 2A.

FIG. 1 is a block diagram of a transducer of an ultrasound imaging system for imaging a body to illustrate the invention. FIG. 2A is a block diagram of an ultrasound imaging system to illustrate a first embodiment of the invention. In reference to FIGS. 1 and 2A, the transducer 12 is excited by a transmit beamformer 14 to propagate ultrasound energy bursts into a body on a scan plane 16. In a manner known to those skilled in the art, the transmit beamformer 14 and receive beamformer 20 are used to electronically steer scan line 18 to cover the entire scan plane 16 to obtain a frame of imaging data for the tissue and/or blood flow in the scan plane. Thus, while the transducer 12 remains stationary relative to scan plane 16, the transmit and receive beamformers 14, 20 are operated to electronically steer scan line 18 across scan plane 16 for imaging tissue and/or blood flow. Techniques for steering a scan line are described, for example, in U.S. Pat. No. 5,148,810.

The B-mode gray scale data acquired comprises a B-mode data frame, and the Doppler signal data so acquired comprises a frame of Doppler data. If displayed in color, the Doppler frame is referred to herein as a frame of color Doppler data. The Doppler data displayed may include energy, mean velocity, variance of velocity estimate or a parameter which is a function of a combination of one or more of the three quantities in various different display modes. A combined mean velocity and energy mode is described, for example, in pending U.S. Pat. application Ser. No. 08/367,064, filed Dec. 30, 1994, entitled "Imaging Modality Showing Energy And Velocity," which is incorporated herein by reference. The receive beamformer 20 supplies the B-mode data to a B-mode data path which includes a B-mode processing unit 22 and the Doppler data to a color Doppler data path which includes an on/off control switch 32, modulator and filter 34 for converting the signal to baseband and to be digitized by A/D converter 36, as well as other components described below.

For blood flow information from the Doppler return to be detected, Doppler components that arise from stationary or slowly moving structures such as vessel walls are removed or reduced by the clutter filters 40 from the digitized output of converter 36. The filtered signals are then sent to a processor 42 which calculates the zero and first order autocorrelation lag values. These values are typically then filtered by temporal filters in color processing unit 44, assuming that autocorrelation values for multiple acoustic frames are available at this point. Then the mean velocity, variance and energy are calculated in the moment calculator 46 using the filtered autocorrelation values for each acoustic frame. This information and the B-mode information from processing unit 22 is then scan-converted by scan converter 48 to be displayed as B-mode and color Doppler information. The scan-converted color Doppler information and the B-mode information is then supplied to monitor 50 for display.

FIG. 2B is a graphical illustration of an EKG waveform 60 to illustrate the operation of the system 10 of FIG. 2A. As shown in FIG. 2B, the EKG waveform 60 includes multiple cardiac cycles, where each cycle includes a R-wave, S-wave, T-wave, P-wave and a Q-wave. The R-wave in the cardiac cycle is the point in time when the heart contracts. Thus, during this point of the cardiac cycle, motion of the heart wall is at a peak value and will generate high amplitude Doppler signals. The portion of the cardiac cycle between the T-wave and the R-wave of the next cardiac cycle is a period known as diastole. During this time period, the heart vessel walls are essentially at rest.

The inventors realized that, by performing color Doppler data acquisition only during diastole (when coronary artery flow is greatest and heart wall motion is at a minimum) and not during the remaining portion of the cardiac cycle, so that the Doppler return during diastole is not mixed with the Doppler information from heart wall motion, it is possible to improve myocardial perfusion detection sensitivity.

In reference to FIG. 2A, an EKG input is supplied from an EKG input unit 62. The EKG waveform from unit 62 is supplied to trigger control 64. Through a suitable user interface, a user can select the portion of the cardiac cycle in reference to the EKG waveform from unit 62 and provide trigger signals to be supplied to on/off control switch 32. Such user interface is known to those skilled in the art and will not be described in detail here.

Thus, in reference to FIGS. 2A and 2B, the user may select the time period (1) between times 72(1) and 74(1) in FIG. 2B to be the time period during which color Doppler data is to be acquired and displayed. This and other similar time periods is referred to herein as a data collection cycle. The acquisition and display of color Doppler data in this manner can occur at any time during an ultrasound imaging session, irrespective of whether or not color Doppler data acquisition has been initiated. In the preferred embodiment, a color Doppler mode is initiated in response to a begin signal. For this purpose, preferably a begin trigger is generated by control unit 64 and provided to switch 32 at time 72(1) to begin the color Doppler data acquisition. At the end 74(1) of the data collection cycle (1), an end trigger is provided by control 64 to switch 32 to switch off the color Doppler data path. In this manner, the color Doppler data is acquired during data collection cycle (1) when heart wall motion is at a minimum, where such Doppler data can be displayed distinct from Doppler data from tissue and/or blood flow at instances in other time periods. The above described process can be repeated for additional data collection cycles (2) through N to show continuous images over several cardiac cycles, N being a positive integer. In the preferred embodiment, the on/off control unit 32 may be implemented by a software function for the beamformer, so that the trigger signal from control 64 controls the beamformers 14, 20.

A secondary application of the invention is for color Doppler velocity and energy mapping of the ventricles and preservation of intra-cardiac blood pool images at end-diastole. During the period known as left ventricular diastole, the Doppler velocity falls to zero or close to zero so that it is difficult to detect. This lack of velocity display at diastole is distracting and results in a poorly defined blood pool. However, by application of the new imaging technique outlined above, the ventricular diastole period frame average color Doppler data can be selected and the information content can be temporally persisted. This results in improved myocardial border estimations. This also prevents color from disappearing in the display which is distracting to the clinician. Such change in system parameters is described in more detail below in reference to FIGS. 3A, 3B.

As noted above, the above described data acquisition can be performed during the data collection cycles (1) through (N) over N cardiac cycles. B-mode data acquisition and display is active and continuous to provide B-mode information in a manner unaffected by the begin and end triggers. As also noted above, the color Doppler information disclosed may include mean velocity, energy, variance or a parameter which is a function of any one or a combination of mean velocity, energy and variance. From FIG. 2B it is noted that no color image is displayed except during the data collection cycles.

The value of N may be set from input by a user or preset in the ultrasound system. As used herein, when the B-mode is indicated to be "active and continuous," this means that B-mode data is continuously acquired and displayed as soon as acquired and processed by unit 22 and converter 48; in other words, the B-mode data is displayed in real time. When color Doppler data is displayed as soon as acquired and processed, the color Doppler data is said to be displayed in real time.

Figure 3A:
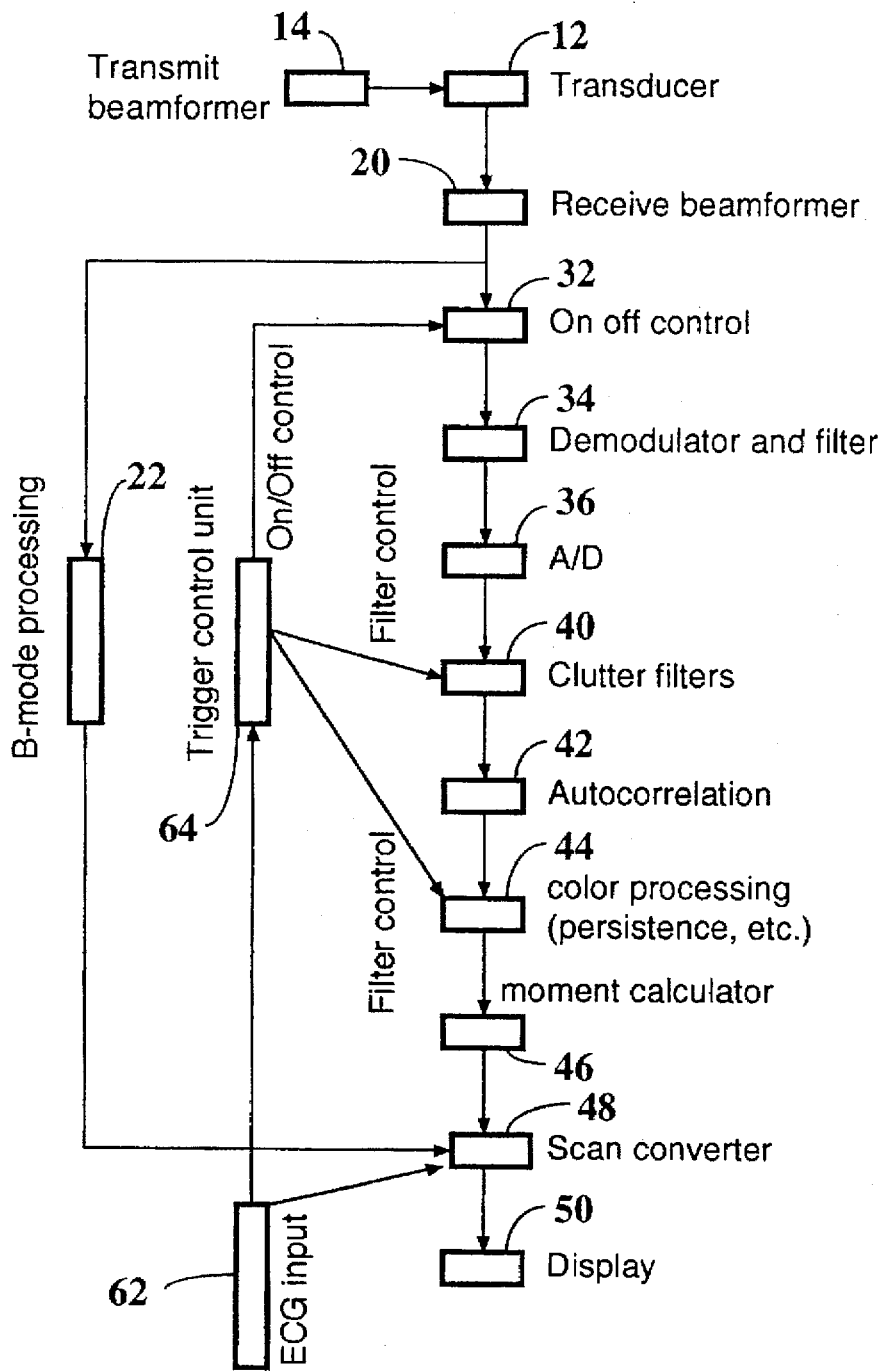
FIG. 3A is a block diagram of an ultrasound imaging system for imaging tissue and blood flow to illustrate a second embodiment of the invention.
Figure 3B:
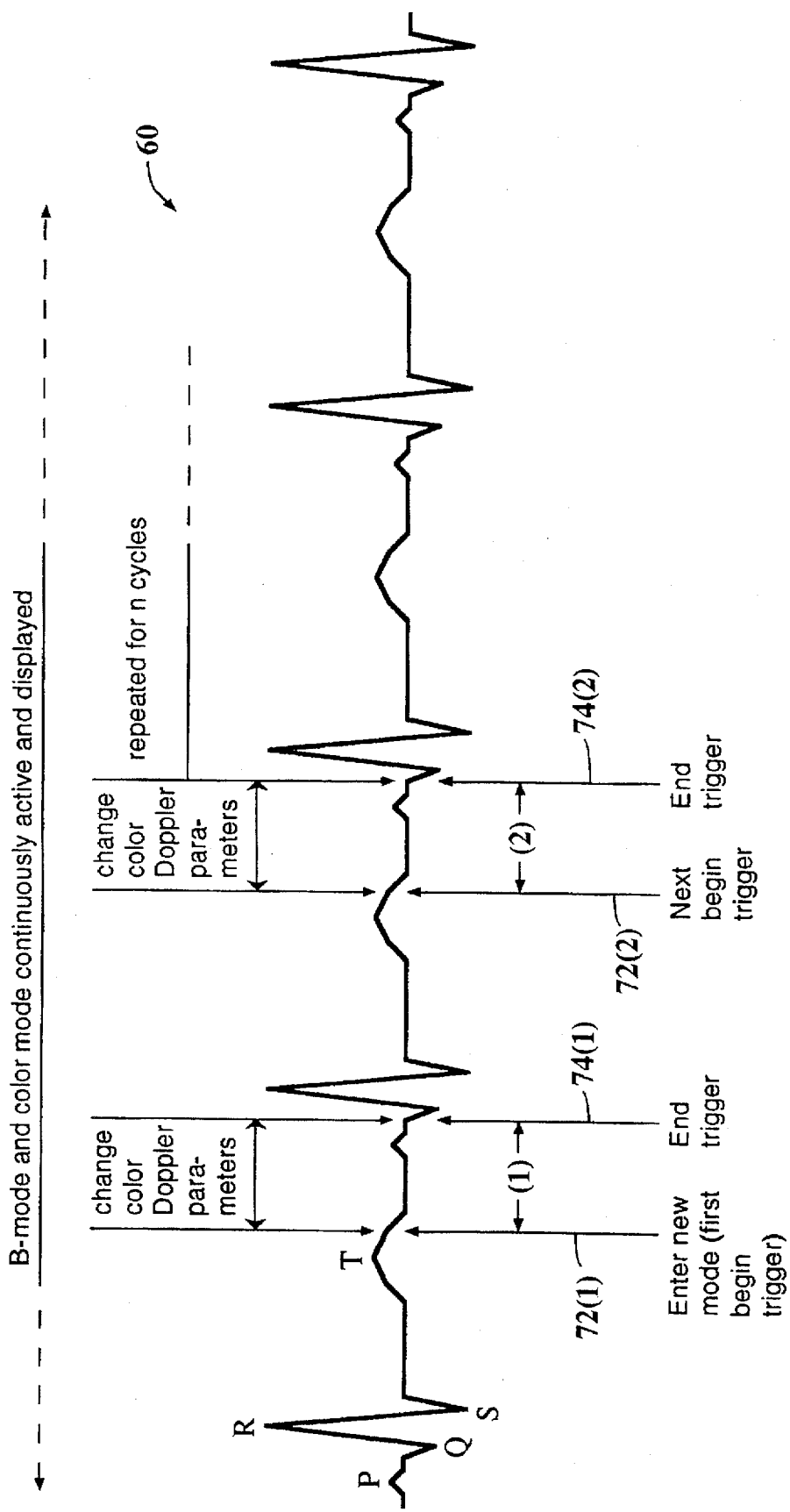
FIG. 3B is a graphical illustration of the EKG waveform for illustrating the operation of the system of FIG. 3A.

In order to improve sensitivity of the system for detecting myocardial perfusion, it may be desirable to change the system parameters, such as by essentially reducing the filtering action by clutter filters 40 of the Doppler signal. This is illustrated in FIGS. 3A, 3B. In reference to FIGS. 2A, 3A, system 100 of FIG. 3A differs from system 10 of FIG. 2A only in that the trigger control unit 64 also provides control signals to clutter filters 40; these signal paths are not present in system 10 of FIG. 2A. In reference to FIG. 3B, both B-mode and color acquisition are always active and only the system parameters in the color processing signal path respond to the triggers. As in the case of system 10, the user through a suitable user interface may select a particular point or points in the cardiac cycle (or any portion of the cycle less than a complete cycle) in order to generate trigger signals for triggering the change in system parameters in system 100. At time 72(1), for example, a begin trigger may be generated by unit 64 to change the filter coefficients applied by clutter filters 40 and the spatial and/or temporal filters in color processing unit 44 to enhance sensitivity and accuracy of detection. In the time period between times 72(1) and 74(1) the heart walls are essentially stationary. Hence, heart wall movement will be at a minimum and the coronary artery flow is at its maximum. For this reason, the filter coefficients of clutter filters 40 may be altered to remove or reduce the effect of the filters 40 in order to enhance sensitivity of detection. At time 74(1), the filter coefficients of filters 40 may be restored to apply effective clutter filtering to the color Doppler signals.

The trigger control unit 64 also provides control signals to the color processing unit 44 to alter the coefficients of the temporal filters in unit 44 in order to temporally persist information at end-diastole at time 74(1). This will improve myocardial border estimations in blood pool measurements and prevent the color Doppler velocity signal from falling to zero.

More than one set of begin and end triggers may be employed to independently control multiple functions and multiple parameters. For instance, one set of triggers could be set along the EKG waveform at the beginning of diastole to change temporal persistence parameters and the end trigger positioned at end diastole to terminate persistence behavior as described above. Another set of triggers positioned along the same EKG waveform would control a different set of behaviors during systole. The systole trigger could be used to modify a new or different level of persistence behavior optimized for the systole time frame.

A signal path is also provided between unit 64 and on/off control switch 32 in system 100, so that unit 64 may generate begin as well as end triggers for controlling the time period during which a color Doppler mode is initiated, by enabling or disabling the Doppler signal path. Such and other variations are within the scope of the invention.

Figure 4A:
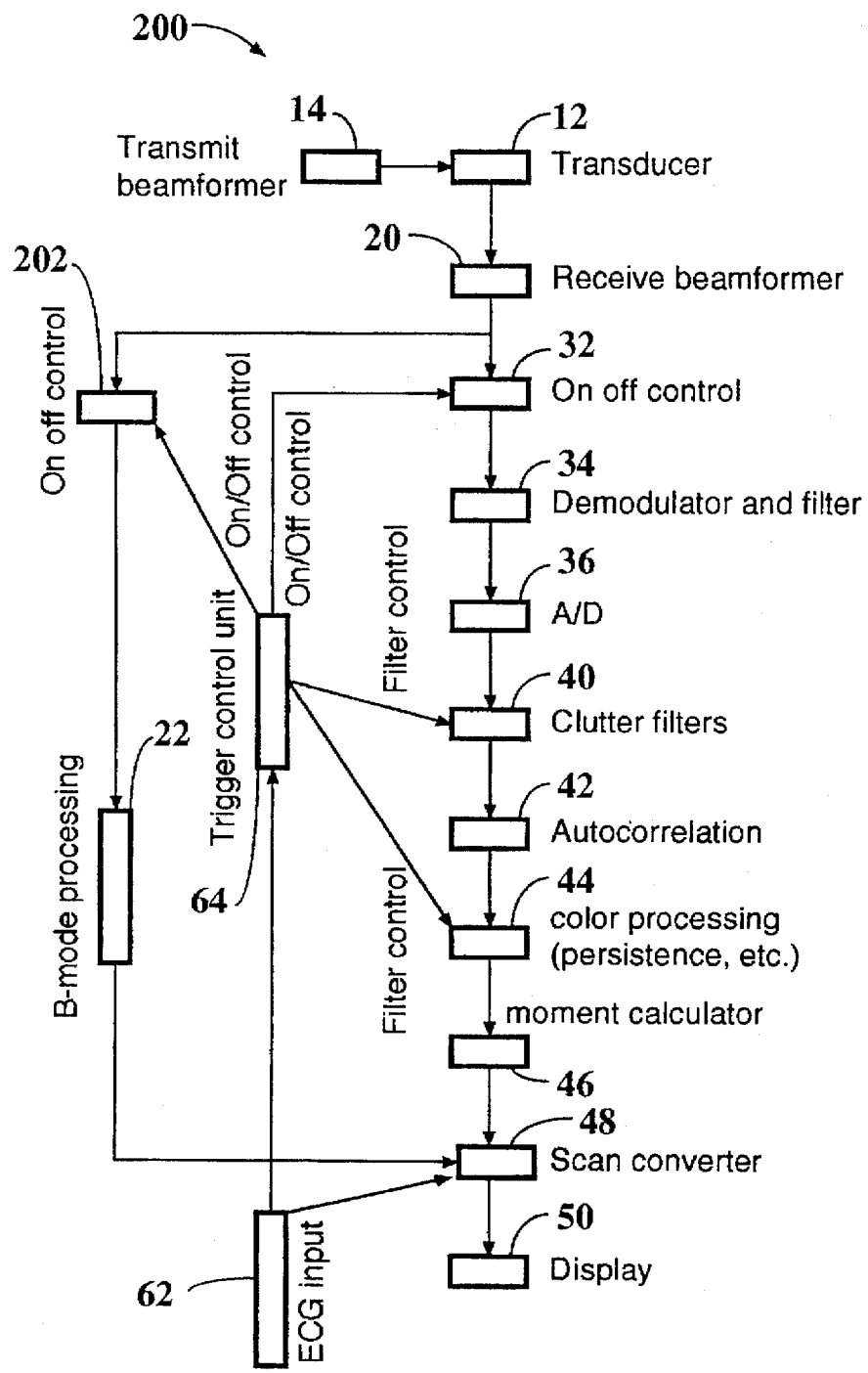
FIG. 4A is a block diagram of an ultrasound imaging system for imaging tissue and blood flow to illustrate a third embodiment of the invention.

FIG. 4A is a block diagram of an ultrasound imaging system 200 to illustrate a third embodiment of the invention. System 200 differs from system 100 of FIG. 3A in that an on off control unit 202 is employed in the B-mode data path and a control signal path is provided between control unit 64 and unit 202 so that B-mode data acquisition and display may be controlled as a function of particular trigger times or time periods selected by the user. In addition, in the control path between unit 64 and color processing unit 44, control unit 64 is capable of controlling the processing unit 44 so that unit 44 monitors and compares the incoming Doppler data sample to the stored prior sample. If a subsequent sample value (such as mean velocity, energy, variance or a parameter that is a function of any one or more of the three quantities) is of a greater amplitude than a previously acquired sample value at a spatial location, it is used to replace the previous sample value to be displayed. But if the subsequent sample value is not of a greater amplitude than a previously acquired sample value, then the previously acquired sample value is retained instead for display. In this manner the highest sample value is accumulated in a sequence of accumulated frames and the display 50 displays the accumulated frames. This enhances the detection of weak motion in the body imaged. The different modes of operation of system 200 are illustrated below in reference to FIGS. 4B–4D.

Figure 4B:
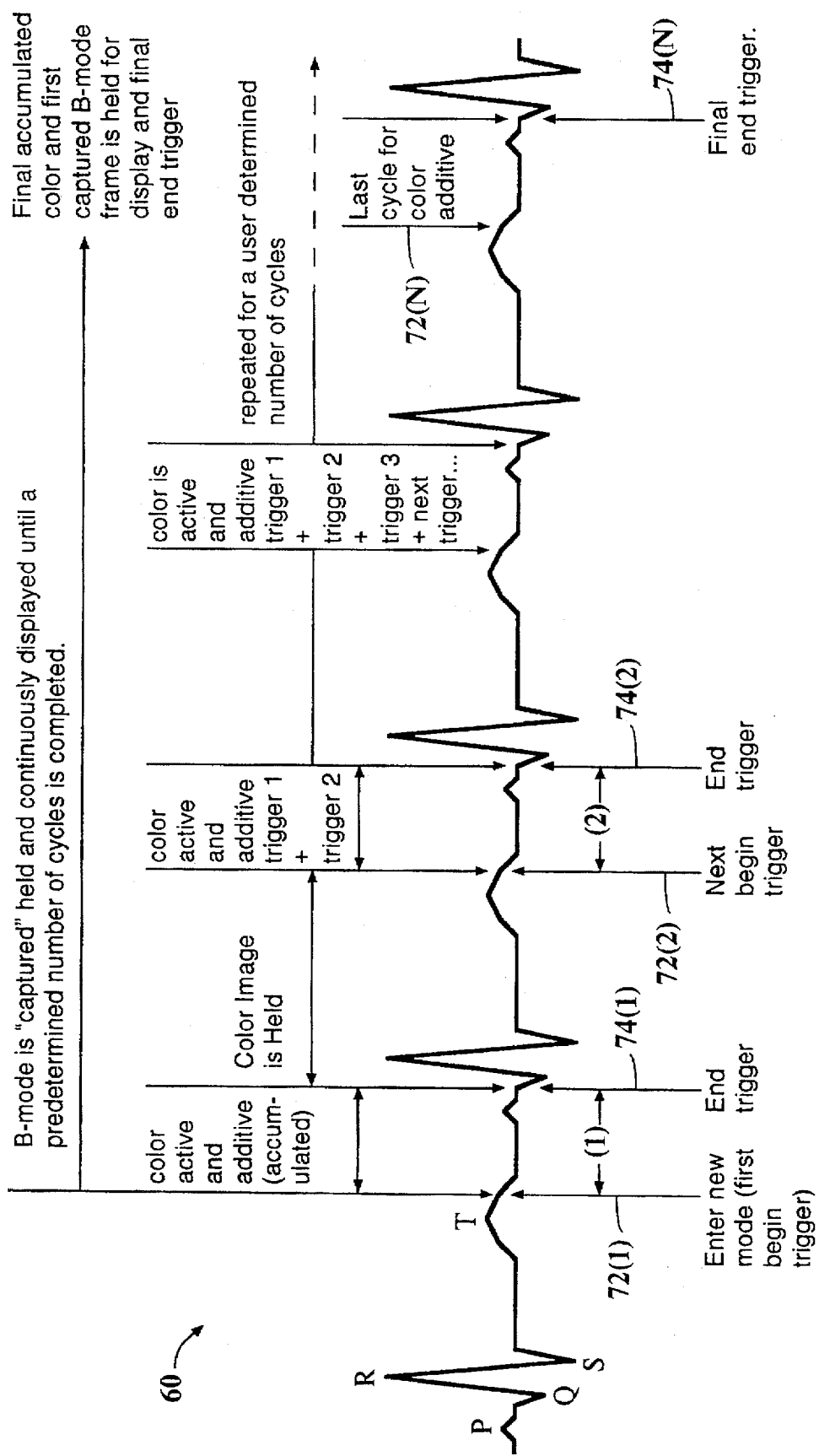

FIG. 4B is a graphical illustration of EKG waveform 60 to illustrate one mode of operation of system 200 of FIG.

4A. Trigger control unit 64 supplies a first begin trigger 72(1) to switch 32 so as to enable the acquisition of color Doppler data. At the same time, unit 64 also sends a begin trigger to on/off control unit 202 to enable the acquisition of a B-mode frame after which the B-mode data path is automatically turned off by control unit 202. B-mode processing unit 22 supplies such captured B-mode frame to scan converter 48 so that such frame is displayed continuously until a predetermined number of cycles have been completed. Control unit 64 may also be used to supply control signals to control the coefficients of clutter filters 40 and the spatial and temporal filters in unit 44 in the manner described above in reference to FIGS. 3A, 3B.

In addition, control unit 64 may also be used to send a control signal to unit 44 in order to combine at least some of the multiple frames of color Doppler data to obtain a sequence of accumulated frames in the manner described above. Thus, if a sample value (such as mean velocity, energy, variance or a parameter that is a function of any one or more of the three quantities) at a spatial location in the subsequent incoming frame is of a greater amplitude than the sample value of a previously acquired frame, it is used to replace the sample value of a previously acquired frame to be displayed. But if the sample value of the subsequent incoming frame is not of a greater amplitude than a previously acquired sample value, then the sample value of the previously acquired frame is substituted for the sample value of the incoming frame for display. This process is repeated for all locations of the frame and the resulting frame is called an "accumulated frame." Hence, each accumulated frame contains pixel values that are the up-to-date highest values at each spatial location. This process is referred to in this application as "additive," and the frames that result from such operation is referred to as accumulated frames. Such process defines a combining step for the incoming frame and the previously acquired frame. In the preferred embodiment, such combining step is performed for at least some of the multiple frames of the color Doppler data to obtain accumulated frames with the highest pixel values of the multiple frames. From the operation, a sequence of accumulated color Doppler data frames is obtained.

As also shown in FIG. 4B, throughout the N data collection cycles, color Doppler data acquisition is performed and the acquisition of color Doppler data is additive. Between the end trigger of one data collection cycle and the begin trigger of the next data collection cycle, the last color Doppler data frame acquired during the last data collection cycle displayed on the display 50 is continuously displayed and held unchanged. As also shown in FIG. 4B, the color Doppler data acquired is additive over the N data collection cycles until the final end trigger 74(N) is reached. In other words, at the begin trigger 72 (2), color processing unit 44 still stores the last color Doppler frame that was acquired during the data collection cycle (1). After the first frame of the data collection cycle (2) has been acquired in response to the begin trigger at time 72 (2), unit 44 then compares the pixel values of such frame to the pixel values of the frame stored to obtain an additively accumulated frame in the manner described above. This process is also performed at the beginning of each of the subsequent data collection cycles so that the color Doppler data is additive over all N-cycles in FIG. 4B, and only the highest pixel values that occur at any point during the N-data collection cycles are displayed. This is particularly advantageous for detecting weak signals such as myocardial perfusion. This increases the concentration of color Doppler signal available for display and is important for collection and reinforcement of color data of blood flow over poorly perfused tissue segments within the heart.

The embodiment of FIG. 4B is particularly useful when the patient is able to hold his breath and lay motionless for a prolonged duration over several cardiac cycles. This is the case since the B-mode image first acquired is held and continuously displayed over several cardiac cycles. The embodiment of FIG. 4C differs from that of FIG. 4B in that the color Doppler data is additive only during a single data collection cycle and that both the color Doppler data and the B-mode data in the frame are refreshed upon the begin trigger of each of the N-data collection cycles. The embodiment of FIG. 4C is advantageous for patients who cannot rest comfortably or quietly, such as uncooperative patients or small children. Extraneous motion is less of a problem because the data is refreshed with each new begin trigger of a new data collection cycle. Thus, upon the begin trigger at time 72 (2), the previously stored color Doppler data as well as B-mode data in the last frame of the prior data collection cycle are replaced by that acquired in response to the begin trigger of the second data collection cycle (2). As in the embodiment of FIG. 4B, during the interim time periods between data collection cycles, the last frame (both B-mode and color Doppler data) of the prior data collection cycle is held static and displayed by display 50 until the time of the begin trigger of the next data collection cycle.

The embodiment of FIG. 4D differs from that of FIG. 4C only in that instead of refreshing the B-mode frame only upon receiving the begin trigger of each data collection cycle, the B-mode is continuously active and displayed in real time.

SUMMARY OF CHARACTERISTICS OF THE OPERATION MODES IN FIGS. 2B, 3B, 4B–4D

I. FIG. 2B
1. Image tissue and fluid
   A. B-mode behavior—B-mode is active and continuous (real time) throughout the cardiac cycle regardless of triggers
2. Begin-trigger
   A. Enters color Doppler mode and is active and displayed until the end-trigger point is reached
3. End-trigger
   A. Exits color Doppler mode and no color Doppler is displayed until next begin trigger
4. Final and Exit Trigger
   A. Begin—End sequence is repeated for n cycles until the trigger is exited By turning on and off color Doppler in this manner, the user is able to look on at the myocardial tissue blood flow at a specific segment in the cardiac cycle. This will eliminate most extraneous color Doppler noise created by myocardial tissues and chamber blood flow. (Note: in this mode the color Doppler is only turned on and off during the cardiac cycle.)

II. FIG. 3B
1. Image tissue and fluid
   A. B-mode behavior—B-mode is active and continuous (real time) throughout the cardiac cycle regardless of triggers
   B. Color behavior—color Doppler is active and continuous (real time) throughout the cardiac cycle but in addition, modifies selected parameters from trigger begin and end points 2. Begin-trigger
   A. Enter selected color Doppler mode
   B. Modify one or more color Doppler parameters including but not limited to:
      a. persistence
      b. Doppler baseline
      c. pre-processing
      d. post-processing
      e. gate or filters
      f. other Doppler parameters
3. End-trigger
   A. At end-trigger return to pre-trigger state.
4. Final and Exit trigger
   A. Being—End sequence is repeated for n cycles until the trigger is exited by user In this situation, both the B-mode and color Doppler are allowed to remain on continuously throughout the entire cardiac cycle. In this configuration, certain selectable color Doppler parameters are modified for specific segments of the cardiac cycle. This provides a greater control of color parameters than previously possible. This gives the user the ability to match the temporal qualities of the heart with the temporal characteristics of the imaging device.

This will be useful in examining blood pools (cardiac chambers), coronary artery flows, and tissue (myocardial) blood flows.

The Doppler baseline can be changed in response to the direction of the blood flow, allowing an increase in the color alias limits imposed by having the baseline in the center of the color map. (With baseline position switching from top to bottom of scale, the Doppler's effective Nyquist limit has been increased.)

III. FIG. 4B
   1. Image tissue and fluid
      A. B-mode behavior
         a. Acquire 1 B-mode frame at begin-trigger and hold displayed image on video screen at begin trigger
         b. Hold captured video frame across all subsequent trigger begin and end points
      B. Color Doppler mode behavior
         a. At begin-trigger, activate color Doppler and accumulate color Doppler information while the trigger is active
         b. At end-trigger, color Doppler mode is held static at point of exit trigger along with the B-mode information
      C. Next trigger cycle
         a. At next begin-trigger, reactivate color Doppler mode and add newly acquired color Doppler information to previously captured and held B-mode and color Doppler frame
      D. Exit trigger cycle
         a. Trigger is exited after a predetermined number of cycles as selected by the user
         b. Final acquired image is held and displayed as a static video frame This allows an accumulation of color Doppler signals over time, thereby increasing the concentration of color Doppler signal available for display over tissue. This is important for collection and reinforcement of color data over poorly perfused tissue segments within the heart.

This is useful when the patient is able to hold his breath and lay motionless for a prolonged duration over several cardiac cycles.

IV. FIG. 4C
   1. Image tissue and fluid
      A. B-mode behavior
         a. Begin-trigger B-mode frame is frozen and held static on the video display until next begin-trigger (at which time the B-mode is refreshed and new B-mode image is acquired)
      B. Color Doppler mode behavior
         a. At begin-trigger, activate color Doppler and accumulate color Doppler information while trigger is active (until end-trigger)
         b. At end-trigger, both color Doppler and the acquired B-mode are held static until the next begin-trigger
         c. Next begin-trigger, acquire new B-mode (refresh B-mode) and acquire new color Doppler (refresh color Doppler)
      Exit trigger cycle
         a. Trigger is exited after a predetermined number of cycles as selected by the user or n cycles until user manually exits the mode
         b. Final acquired image is held and displayed as a static video frame This also allows an accumulation of color Doppler signals over time and increases the concentration of color Doppler signal available for display over tissue. However, the advantage here is that the B-mode and color Doppler are refreshed with each new begin trigger. This reduces the effect that motion translation artifact has on subsequent images.

This is useful in a patient that cannot rest comfortably or quietly; uncooperative patients or small children. Extraneous motion is less of a problem for this configuration because the data is refreshed with new begin-triggers.

V. FIG. 4D
   1. Image tissue and fluid
      A. B-mode behavior (continuous real-time B-mode)
         a. B-mode is active and continuously displayed regardless of begin and end-trigger points.
      B. Begin-trigger
         a. Activate, accumulate and display color Doppler until end-trigger
      C. End-trigger
         a. Exit color Doppler mode and do not display or hold accumulated color Doppler information on the video display
      D. Next begin-trigger
         a. Repeat previously described begin-trigger and end-trigger behavior (step B.a. and step C.a.)
      E. Exit trigger cycle
         a. Trigger is exited after a predetermined number of cycles as selected by the user or n cycles until user manually exits the mode In this case, the B-mode is always active and in real-time. This allows for the greatest amount of patient motion with lesser artifacts. This is useful for the myocardial tissue blood flow and coronary artery flow.

In General

Out of all the configurations, those of FIGS. 3B and 4D are particularly preferred: that of FIG. 3B in regard to control of imaging parameters and that of FIG. 4D in its ability to gather tissue blood flow information for a given cardiac segment. The continuous B-mode acquisition in the case of FIG. 4D will be the most intuitive for clinical customers.

While in the embodiments described above, each data collection cycle occurs at the same position of the cardiac cycle, (that is, at constant relative timing relationship to a particular point in the cardiac cycles, such as the R-wave), it will be understood that this is not required. If desired, such data collection cycles may occur over different portions of the cardiac cycles and two or more data collection cycles can occur within the same cardiac cycle. Such and other variations are within the scope of the invention. Furthermore, multiple trigger signals at any number of user selectable points of the cardiac cycle may be employed to change color Doppler or B-mode imaging parameters. This would be most important in the FIGS. 2B and 3B imaging protocols described above.

While begin and end triggers are used to control the color Doppler data acquisition as well as, in some cases, the B-mode data acquisition in the embodiments described above, it will be understood that other methods for control and for specifying data collection cycles may be used and are within the scope of the invention. For example, a begin trigger may be used to initiate color Doppler data acquisition in the same manner as described above, but such acquisition may be ended at a predetermined time after the begin trigger, instead of at a time when an end trigger is received as described above. Such predetermined time period may be the same or different for the N data collection cycles.

Instead of using the EKG waveform for deriving a trigger, other signals indicative of a cardiac cycle may be used for this purpose, such as signals derived from phonocardiogram, pressure wave, pulse wave or respiratory signal waveforms. Other waveforms that can be used to produce a trigger include a pulse wave or continuous wave Doppler, m-mode strip display, and all physio recording devices including; pulse pressure wave forms, heartsound waveforms, and respiratory waveforms. The advantage of any such triggers over, for example, triggers determined by user input is that such triggers avoid the variability that would be associated with user-determined triggers of points in a cardiac cycle.

In the preferred embodiment described above, at least some of the multiple frames of the color Doppler data are compared to obtain accumulated frames with the highest pixel values of the multiple frames. Such operation is referred to above as "additive" and the frames that result from such operation is referred to as an accumulated frame. It will be understood, however, that the multiple frames of the color Doppler data may be combined in other ways to optimize the data acquisition and display and to obtain accumulated frames. Such and other variations are within the scope of the invention.

While the invention has been described above by reference to various embodiments, it will be understood that different changes and modifications may be made without departing from the scope of the invention which is defined only by the appended claims and their equivalents.

What is claimed is:

1. An ultrasound method for imaging tissue and/or blood flow, comprising the steps of:
   providing a begin trigger indicative of a first point in a cardiac cycle; and
   acquiring in response to the begin trigger a color Doppler first imaging sequence of multiple frames of color Doppler data at different times in said cardiac cycle.

2. The method of claim 1, further comprising:
   providing a stop trigger indicative of a second point in the cardiac cycle; and
   stopping the acquisition of color Doppler data in response to the stop trigger.

3. The method of claim 2, said providing steps providing consecutive N pairs of begin and stop triggers occurring in the same or different cardiac cycles, each pair defining a data collection cycle.

4. The method of claim 3, wherein said providing steps provide the begin and end triggers at a constant relative timing relationship to R-waves of the N cardiac cycles.

5. The method of claim 3, further comprising the step of a user inputting a value for N, or presetting a value for N in an ultrasound system.

6. The method of claim 3, further comprising displaying the multiple frames of color Doppler data acquired.

7. The method of claim 6, said displaying step displaying the multiple frames of color Doppler data acquired in real time during the data collection cycles, wherein no color Doppler data is displayed outside of the data collection cycles.

8. The method of claim 3, further comprising the steps of:
   combining at least some of the multiple frames of color Doppler data in the first sequence to obtain a second sequence of accumulated frames; and
   displaying the second sequence of accumulated frames.

9. The method of claim 8, said combining step including comparing said at least some of the multiple frames of color Doppler data to obtain accumulated frames so that each of the accumulated frames contains pixel values that are up-to-date highest values.

10. The method of claim 9, said combining step comparing the multiple frames acquired continually over the N data collection cycles when such frames are being acquired to obtain said second sequence of accumulated frames, said displaying step displaying said second sequence of accumulated frames in said N data collection cycles.

11. The method of claim 8, said combining step successively combining the multiple frames acquired during each of the data collection cycles in real time to obtain a corresponding second sequence of accumulated frames for each of the data collection cycles, said displaying step displaying each of said sequences of accumulated frames during the corresponding data collection cycle.

12. The method of claim 11, said displaying step displaying between the stop trigger of a prior data collection cycle and the begin trigger of the next data collection cycle the last accumulated frame in the sequence for the prior data collection cycle.

13. The method of claim 3, wherein said providing step is such that each of the N data collection cycles occurs in a portion of a different cardiac cycle, said N data collection cycles occurring in the same portion of N consecutive cardiac cycles.

14. The method of claim 3, further comprising the steps of acquiring B-mode data and displaying the B-mode and color Doppler data during said N data collection cycles.

15. The method of claim 14, said acquiring step acquiring one frame of B-mode data in response to the begin trigger of the first data collection cycle.

16. The method of claim 15, wherein said displaying step displays said multiple frames of color Doppler data in real time and said frame of B-mode data during the N data collection cycles.

17. The method of claim 14, said acquiring step acquiring a frame of B-mode data in response to the begin trigger of each of the data collection cycles, and wherein said displaying step displays said multiple frames of color Doppler data in real time and substantially continuously displays said frame of B-mode data during each of the N data collection cycles.

18. The method of claim 14, wherein said acquiring step acquires frames of B-mode data continually and said displaying step displays said frames of B-mode data in real time during the N data collection cycles.

19. The method of claim 1, said providing step including deriving the begin trigger from an EKG, phonocardiogram, pressure wave, pulse wave or respiratory signal waveform.

20. The method of claim 19, said acquiring step including electronically steering a scan line across said tissue and/or blood flow to acquire said frames.

21. The method of claim 19, further comprising:
providing a stop trigger indicative of a second point in the cardiac cycle; and
stopping the acquisition of color Doppler data in response to the stop trigger.

22. The method of claim 21, said providing steps providing consecutive N pairs of begin and stop triggers occurring in the same or different cardiac cycles, each pair defining a data collection cycle.

23. The method of claim 22, wherein said providing steps provide the begin and end triggers at a constant relative timing relationship to R-waves of the N cardiac cycles.

24. The method of claim 22, further comprising the steps of acquiring B-mode data and displaying the B-mode and color Doppler data during said N data collection cycles.

25. The method of claim 24, said acquiring step acquiring one frame of B-mode data in response to the begin trigger of the first data collection cycle.

26. The method of claim 25, wherein said displaying step displays said multiple frames of color Doppler data in real time and said frame of B-mode data during the N data collection cycles.

27. The method of claim 24, said acquiring step acquiring a frame of B-mode data in response to the begin trigger of each of the data collection cycles, and wherein said displaying step displays said multiple frames of color Doppler data in real time and substantially continuously displays said frame of B-mode data during each of the N data collection cycles.

28. The method of claim 24, wherein said acquiring step acquires frames of B-mode data continually and said displaying step displays said frames of B-mode data in real time during the N data collection cycles.

29. An ultrasound method for imaging tissue and/or blood flow, comprising the steps of:
providing a trigger responsive to a portion of a cardiac cycle, said portion being shorter than the cardiac cycle;
displaying in response to the trigger a color Doppler first imaging sequence of multiple frames of color Doppler data of different times in said cardiac cycle.

30. The method of claim 29, said providing step providing a begin and a stop trigger to indicate said portion of the cardiac cycle, said displaying step displaying said multiple frames of color Doppler data in response to the begin trigger and stopping the display of color Doppler data in response to the stop trigger.

31. The method of claim 30, said providing step providing consecutive N pairs of begin and stop triggers occurring in the same or different cardiac cycles, each pair forming a data collection cycle, wherein said displaying step displays multiple frames of said color Doppler data during such cycles, N being a positive integer.

32. The method of claim 31, further including the step of a user inputting a value for N, or presetting a value for N in an ultrasound system, said displaying step displaying said multiple frames of color Doppler data in response to each begin trigger and stopping the display of color Doppler data in response to each stop trigger.

33. The method of claim 31, wherein said providing step provides the begin and end triggers at a constant relative timing relationship to R-waves of the N cardiac cycles.

34. The method of claim 33, said displaying step displaying the multiple frames of color Doppler data acquired in real time during the data collection cycles, wherein no color Doppler data is displayed outside of the data collection cycles.

35. The method of claim 30, further comprising the steps of:
combining at least some of the multiple frames of color Doppler data to obtain a sequence of accumulated frames; and
wherein said displaying step displays the sequence of accumulated frames.

36. The method of claim 35, said combining step successively combining the multiple frames acquired continually over the N data collection cycles when such frames are being acquired to obtain a sequence of accumulated frames, said displaying step displaying said sequence of accumulated frames in said N data collection cycles.

37. The method of claim 35, said combining step successively combining the multiple frames acquired during each of the data collection cycles in real time to obtain a corresponding sequence of accumulated frames for each of the data collection cycles, said displaying step displaying each of said sequences of accumulated frames during the corresponding data collection cycle.

38. The method of claim 37, said displaying step displaying between the stop trigger of a prior data collection cycle and the begin trigger of the next data collection cycle the last accumulated frame in the sequence for the prior data collection cycle.

39. The method of claim 30, wherein said providing step is such that each of the N data collection cycles occurs in a portion of a different cardiac cycle, said N data collection cycles occurring in the same portion of N consecutive cardiac cycles.

40. The method of claim 30, further comprising the steps of acquiring B-mode data and displaying the B-mode and color Doppler data during said N data collection cycles.

41. The method of claim 40, said acquiring step acquiring a frame of B-mode data in response to the begin trigger of the first data collection cycle.

42. The method of claim 41, wherein said displaying step displays said multiple frames of color Doppler data in real time and said frame of B-mode data during the N data collection cycles.

43. The method of claim 40, said acquiring step acquiring a frame of B-mode data in response to the begin trigger of each of the data collection cycles, and wherein said displaying step displays said multiple frames of color Doppler data in real time and substantially continuously displays said frame of B-mode data during each of the N data collection cycles.

44. The method of claim 40, wherein said acquiring step acquires frames of B-mode data continually and said displaying step displays said frames of B-mode data in real time.

45. The method of claim 29, said providing step including deriving said trigger from an EKG, phonocardiogram, pressure wave, pulse wave or respiratory signal waveform.

46. The method of claim 45, said acquiring step including electronically steering a scan line across said tissue and/or blood flow to acquire said frames.

47. The method of claim 45, said providing step providing a begin and a stop trigger to indicate said portion of the cardiac cycle, said displaying step displaying said multiple frames of color Doppler data in response to the begin trigger and stopping the display of color Doppler data in response to the stop trigger.

48. The method of claim 47, said providing steps providing consecutive N pairs of begin and stop triggers occurring in the same or different cardiac cycles, each pair defining a data collection cycle, said displaying step displaying said multiple frames of color Doppler data in response to each begin trigger and stopping the display of color Doppler data in response to each stop trigger.

49. The method of claim 48, wherein said providing step provides the begin and end triggers at a constant relative timing relationship to R-waves of the N cardiac cycles.

50. The method of claim 48, further comprising the steps of acquiring B-mode data and displaying the B-mode data together with color Doppler data displayed during said N data collection cycles.

51. The method of claim 50, said B-mode data displaying step displaying step displaying one frame of B-mode data in response to the begin trigger of the first data collection cycle.

52. The method of claim 51, wherein said displaying step displays said multiple frames of color Doppler data in real time and said B-mode data displaying step displaying said one frame of B-mode data during the N data collection cycles.

53. The method of claim 50, said acquiring step acquires and said B-mode data displaying step displaying a corresponding frame of B-mode data in response to the begin trigger of each of the data collection cycles, and wherein said displaying steps displays said multiple frames of color Doppler data in real time and substantially continuously displays said corresponding frame of B-mode data during each of the N data collection cycles.

54. The method of claim 50, wherein said acquiring step acquires frames of B-mode data continually and said B-mode displaying step displays said frames of B-mode data in real time during the N data collection cycles.

55. An ultrasound method for imaging tissue and/or blood flow, comprising the steps of:
acquiring color Doppler data from said tissue and/or blood flow by means of a system with system parameters;
providing a trigger indicative of a point in the cardiac cycle; and
altering the values of said system parameters in response to the trigger so that the acquiring step acquires color Doppler data according to different system parameters at different points of the cardiac cycle.

56. The method of claim 55, said altering step being such that the acquiring step acquires color Doppler data according to different system parameters before and after the trigger.

57. The method of claim 55, said method suitable for imaging a human or animal body, wherein said altering step alters the system parameters during diastole to reduce or remove wall filtering and to increase sensitivity to blood flow.

58. The method of claim 55, said method suitable for imaging human or animal body, said method further including displaying the acquired color Doppler data, wherein said altering step alters the system parameters to preserve a color display of the body during diastole.

59. The method of claim 55, said altering step altering temporal persistence of the system.

60. The method of claim 55, said providing step including deriving said trigger from an EKG, phonocardiogram, pressure wave, pulse wave or respiratory signal waveform.

61. The method of claim 60, wherein said trigger is responsive to a portion of a cardiac cycle, said portion being shorter than the cardiac cycle; and wherein said acquiring step initiates a color Doppler imaging mode in response to the trigger and acquires in said mode within said portion of the cardiac cycle multiple frames of color Doppler data from said tissue and/or blood flow, said multiple frames being acquired at different times in said portion of the cardiac cycle.

62. The method of claim 55, said acquiring step acquiring B-mode and color Doppler data continually, said method further comprising displaying said B-mode and color Doppler data in real time.

63. The method of claim 55, wherein said acquiring step comprises initiating a color Doppler imaging mode in response to the begin trigger and acquiring consecutively in said mode multiple frames of color Doppler data from said tissue and/or blood flow, said multiple frames being acquired at different times in said cardiac cycle, said acquiring step including electronically steering a scan line across said tissue and/or blood flow to acquire said frames.

64. An ultrasound apparatus for imaging tissue and/or blood flow, comprising:
means for providing a begin trigger indicative of a first point in a cardiac cycle; and
means for acquiring in response to the begin trigger a color Doppler first imaging sequence of multiple frames of color Doppler data at different times in said cardiac cycle.

65. An ultrasound apparatus for imaging tissue and/or blood flow, comprising:
means for providing a trigger responsive to a portion of a cardiac cycle, said portion being shorter than the cardiac cycle;
means for displaying in response to the begin trigger a color Doppler first imaging sequence of multiple frames of color Doppler data of different times in said cardiac cycle.

66. An ultrasound system for imaging tissue and/or blood flow, comprising:
means for acquiring color Doppler data from said tissue and/or blood flow using system parameters;
means for providing a trigger indicative of a point in the cardiac cycle; and
means for altering the values of said system parameters in response to the trigger so that the acquiring step acquires color Doppler data according to different system parameters at different points of the cardiac cycle.

67. The apparatus of claim 66, said altering means including a filter processing said acquired ultrasound color Doppler data, said system parameters including a characteristic of the filter, said filter changing its characteristic in response to the trigger.

68. The apparatus of claim 67, said filter being a clutter filter, a persistence filter or a spatial filter.

69. An ultrasound method for imaging tissue and/or blood flow, comprising the steps of:
providing N triggers, each trigger occurring in a corresponding cardiac cycle of N different cardiac cycles, the triggers being provided in response to portions of the N cardiac cycles, wherein said portions begin at substantially the same point in such cycles;
acquiring in response to each of the triggers a color Doppler imaging sequence of multiple frames of color Doppler data in said corresponding cardiac cycle.

70. The method of claim 69, said providing step providing a pair of a begin and a stop trigger to indicate each of said portions of the N cardiac cycles, each pair defining a data collection cycle.

71. The method of claim 70, said method further comprising displaying the color Doppler imaging sequence of multiple frames of color Doppler data acquired in each of some of the N cardiac cycles in response to the begin trigger of a corresponding cardiac cycle, and stopping the display of color Doppler data in response to the stop trigger of said corresponding cardiac cycle.

72. The method of claim 70, wherein said providing step provides the begin and end triggers at a constant relative timing relationship to R-waves of the N cardiac cycles.

73. The method of claim 70, further comprising the steps of acquiring B-mode data and displaying the B-mode and color Doppler data during said N data collection cycles.

74. The method of claim 73, said acquiring step acquiring one frame of B-mode data in response to the begin trigger of the first data collection cycle.

75. The method of claim 74, wherein said displaying step displays said multiple frames of color Doppler data in real time and said frame of B-mode data during the N data collection cycles.

76. The method of claim 73, said acquiring step acquiring a frame of B-mode data in response to the begin trigger of each of the data collection cycles, and wherein said displaying step displays said multiple frames of color Doppler data in real time and substantially continuously displays said frame of B-mode data during each of the N data collection cycles.

77. The method of claim 73, wherein said acquiring step acquires frames of B-mode data continually and said displaying step displays said frames of B-mode data in real time during the N data collection cycles.

78. An ultrasound method for imaging tissue and/or blood flow, comprising the steps of:
 providing a begin trigger indicative of a first point in a cardiac cycle;
 acquiring sequentially and in response to the begin trigger a color Doppler imaging sequence of multiple frames of color Doppler data at different times in said cardiac cycle; and
 displaying said color Doppler imaging sequence of multiple frames of color Doppler data in substantially the same order that they are acquired.

79. The method of claim 78, further comprising:
 providing a stop trigger indicative of a second point in the cardiac cycle; and
 stopping the acquisition of color Doppler data in response to the stop trigger.

80. The method of claim 79, said providing steps providing consecutive N pairs of begin and stop triggers occurring in the same or different cardiac cycles, each pair defining a data collection cycle.

81. The method of claim 80, said method further comprising displaying the color Doppler imaging sequence of multiple frames of color Doppler data acquired in each of some of the N cardiac cycles in response to the begin trigger of a corresponding cardiac cycle, and stopping the display of color Doppler data in response to the stop trigger of said corresponding cardiac cycle.

82. The method of claim 80, wherein said providing steps provide the begin and end triggers at a constant relative timing relationship to R-waves of the N cardiac cycles.

83. The method of claim 80, further comprising the steps of acquiring B-mode data and displaying the B-mode and color Doppler data during said N data collection cycles.

84. The method of claim 83, said acquiring step acquiring one frame of B-mode data in response to the begin trigger of the first data collection cycle.

85. The method of claim 84, wherein said displaying step displays said multiple frames of color Doppler data in real time and said frame of B-mode data during the N data collection cycles.

86. The method of claim 83, said acquiring step acquiring a frame of B-mode data in response to the begin trigger of each of the data collection cycles, and wherein said displaying step displays said multiple frames of color Doppler data in real time and substantially continuously displays said frame of B-mode data during each of the N data collection cycles.

87. The method of claim 83, wherein said acquiring step acquires frames of B-mode data continually and said displaying step displays said frames of B-mode data in real time during the N data collection cycles.

88. An ultrasound system for imaging tissue and/or blood flow, comprising:
 means for providing N triggers, each trigger occurring in a corresponding cardiac cycle of N different cardiac cycles, the triggers being provided in response to portions of the N cardiac cycles, wherein said portions begin at substantially the same point in such cycles; and
 means for acquiring in response to each of the triggers a color Doppler imaging sequence of multiple frames of color Doppler data in said corresponding cardiac cycle.

89. An ultrasound system for imaging tissue and/or blood flow, comprising:
 means for providing a begin trigger indicative of a first point in a cardiac cycle;
 means for acquiring sequentially and in response to the begin trigger a color Doppler imaging sequence of multiple frames of color Doppler data at different times in said cardiac cycle; and
 means for displaying said color Doppler imaging sequence of multiple frames of color Doppler data in substantially the same order that they are acquired.

90. An ultrasound method for imaging tissue and/or blood flow, comprising the steps of:
 providing N triggers, each trigger occurring in a corresponding cardiac cycle of N different cardiac cycles, the triggers being provided in response to portions of the N cardiac cycles; and
 acquiring in response to each of the triggers a color Doppler imaging sequence of multiple frames of color Doppler data in said corresponding cardiac cycle, wherein the acquiring step begins in each cardiac cycle at a substantially constant time after each trigger.

91. An ultrasound system for imaging tissue and/or blood flow, comprising:
 means for providing N triggers, each trigger occurring in a corresponding cardiac cycle of N different cardiac cycles, the triggers being provided in response to portions of the N cardiac cycles; and
 means for acquiring in response to each of the triggers a color Doppler imaging sequence of multiple frames of color Doppler data in said corresponding cardiac cycle, wherein the acquiring step begins in each cardiac cycle at a substantially constant time after each trigger.

* * * * *

UNITED STATES PATENT AND TRADEMARK OFFICE
CERTIFICATE OF CORRECTION

PATENT NO. : 5,709,210
DATED : January 20, 1998
INVENTOR(S) : J. Michael Green et al.    Page 1 of 2

It is certified that error appears in the above-indentified patent and that said Letters Patent is hereby corrected as shown below:

On the Title Page

In column 2, line 11, under "OTHER PUBLICATIONS" replace "Coronoary" with --Coronary--.

In column 2, line 4, under "ABSTRACT" replace "coefficience" with --coefficient--.

In column 2, line 54, after "parameters" insert --;--.

In column 6, lines 42-43, replace "on off" with --on/off--.

In column 10, line 15, before "Exit" insert --C.--.

UNITED STATES PATENT AND TRADEMARK OFFICE
CERTIFICATE OF CORRECTION

PATENT NO. : 5,709,210
DATED : January 20, 1998
INVENTOR(S) : J. Michael Green et al.

It is certified that error appears in the above-indentified patent and that said Letters Patent is hereby corrected as shown below:

In the Claims

In claim 51, line 2, delete "displaying step".

Signed and Sealed this

Third Day of April, 2001

Attest:

NICHOLAS P. GODICI

Attesting Officer

Acting Director of the United States Patent and Trademark Office